US009820766B2

United States Patent
Hartoumbekis et al.

(10) Patent No.: US 9,820,766 B2
(45) Date of Patent: *Nov. 21, 2017

(54) DUAL DIRECTIONAL ARTICULATION HAND INSTRUMENT

(71) Applicant: Covidien LP, Mansfield, MA (US)

(72) Inventors: Elias Hartoumbekis, New Haven, CT (US); Roddi Simpson, Higganum, CT (US); Earl M. Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/551,355

(22) Filed: Nov. 24, 2014

(65) Prior Publication Data

US 2015/0150575 A1 Jun. 4, 2015

Related U.S. Application Data

(60) Provisional application No. 61/911,758, filed on Dec. 4, 2013.

(51) Int. Cl.
*A61B 17/29* (2006.01)
*A61B 17/00* (2006.01)

(52) U.S. Cl.
CPC ........ *A61B 17/29* (2013.01); *A61B 2017/003* (2013.01); *A61B 2017/00323* (2013.01);
(Continued)

(58) Field of Classification Search
None
See application file for complete search history.

(56) References Cited

U.S. PATENT DOCUMENTS

| 5,431,323 A | 7/1995 | Smith et al. |
| 7,862,554 B2 | 1/2011 | Hegeman et al. |

(Continued)

FOREIGN PATENT DOCUMENTS

WO 2013/009699 A2 1/2013

OTHER PUBLICATIONS

European Search Report for EP 14196152 dated May 7, 2015.
European Office Action issued in European Appln. No. 14196152.4 dated Feb. 7, 2017.

*Primary Examiner* — Lynsey Eiseman
*Assistant Examiner* — Qingjun Kong

(57) ABSTRACT

A surgical device for performing surgery includes a handle assembly, an elongate member extending from the handle assembly, an articulation mechanism, and an adapter. The elongate member has articulating and straight sections. The articulating section is configured to articulate with respect to the straight section. The adapter rotatably couples the elongate member with the articulation mechanism such that when the elongate member is in a first rotational orientation with respect to the articulation mechanism, the articulating section articulates toward a first direction relative to the straight section upon movement of the handle assembly towards the first direction with respect to the straight section and when the elongate member is in a second rotational orientation with respect to the articulation mechanism, the articulating section articulates toward a second direction relative to the straight section upon movement of the handle assembly towards the first direction with respect to the straight section.

12 Claims, 11 Drawing Sheets

(52) U.S. Cl.
CPC . *A61B 2017/291* (2013.01); *A61B 2017/2905* (2013.01); *A61B 2017/2927* (2013.01); *A61B 2017/2929* (2013.01)

(56) References Cited

U.S. PATENT DOCUMENTS

| | | | |
|---|---|---|---|
| 2005/0096694 A1 | 5/2005 | Lee | |
| 2007/0158385 A1 | 7/2007 | Hueil et al. | |
| 2009/0299344 A1* | 12/2009 | Lee | A61B 17/062 606/1 |
| 2010/0030018 A1* | 2/2010 | Fortier | A61B 17/29 600/104 |
| 2012/0095451 A1* | 4/2012 | Hegeman | A61B 1/0055 606/1 |

* cited by examiner

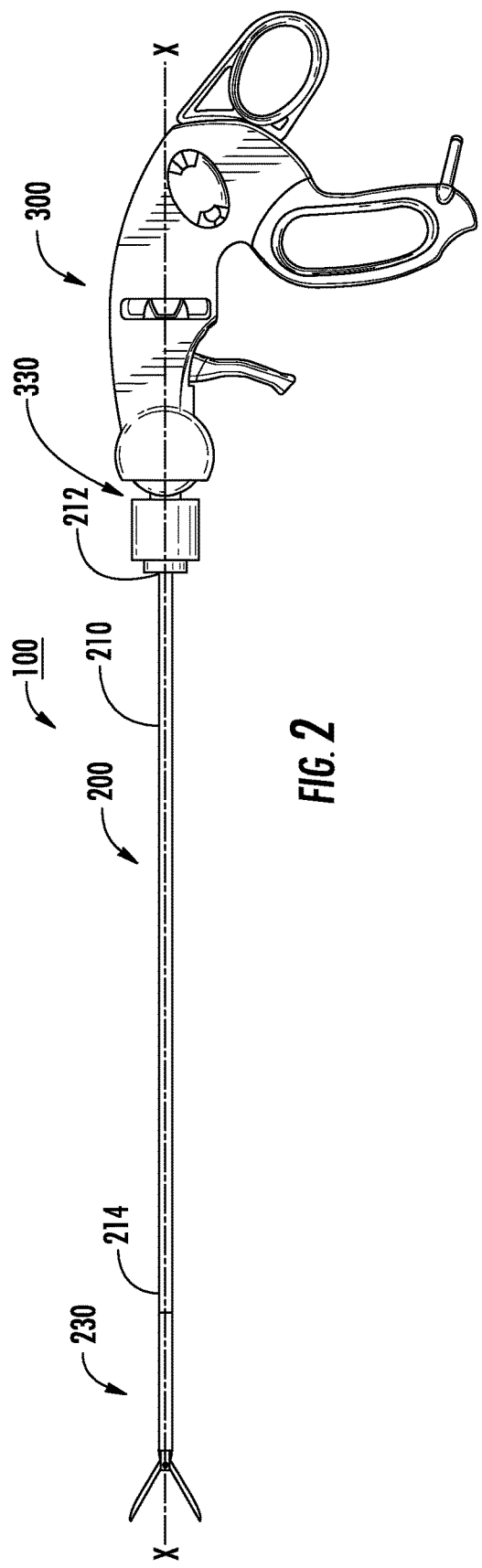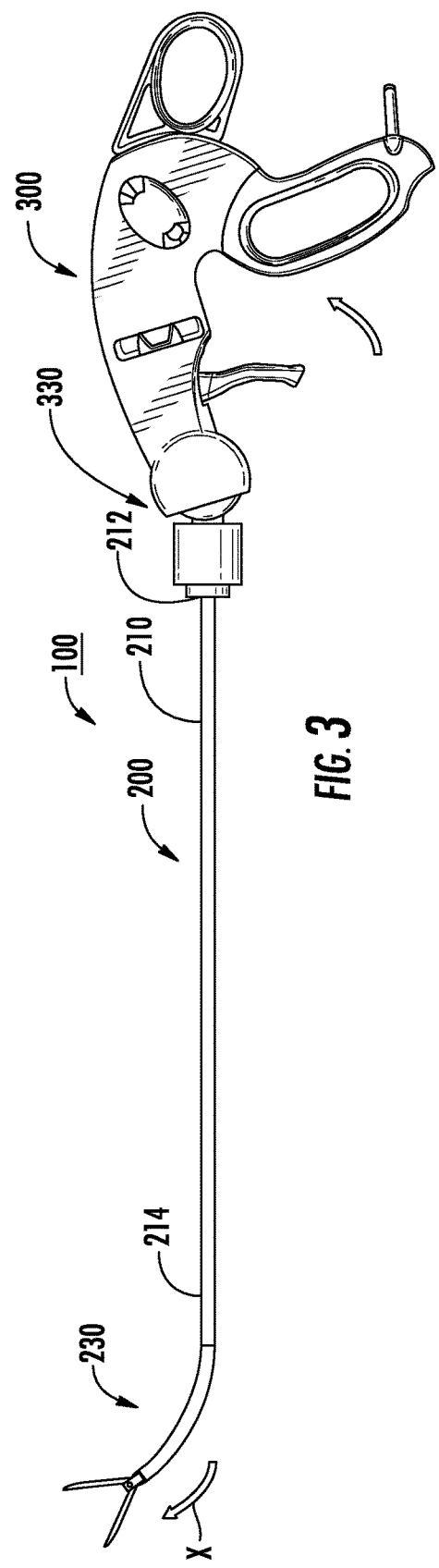

DUAL DIRECTIONAL ARTICULATION HAND INSTRUMENT

CROSS-REFERENCE TO RELATED APPLICATIONS

This application claims the benefit of and priority to U.S. Provisional Patent Application No. 61/911,758, filed Dec. 4, 2013, the entire disclosure of which is incorporated by reference herein.

BACKGROUND

Technical Field

The present disclosure relates to a surgical instrument, and more particularly, to a surgical instrument including an articulating section selectively articulatable in a direction of a movement of a handle assembly or a direction opposite of the movement of the handle assembly.

Background of Related Art

Various surgical procedures are performed in a minimally invasive manner. This includes forming a small opening through a body wall of a patient, e.g., in the abdomen, and inserting surgical instruments therethrough to perform surgical procedures. The surgical instruments may be inserted through naturally occurring orifices of the patient. Due to the relatively small interior dimensions of the access devices used in endoscopic procedures, only elongated, small-diametered instrumentation may be used to access the internal body cavities and organs. Typically, endoscopic surgery is conducted by inserting a number of ports through small incisions in the patient's skin or naturally occurring openings to access a surgical site. One of the ports receives an endoscope. The surgeon views the surgical site via the endoscope and performs the surgery by inserting various surgical devices into the patient through the ports. For example, the surgeon may insert a hand operated endoscopic grasper, a dissector, shears, scissors and the like. This technique does not require "opening up" the patient, resulting in less invasive surgery than conventional procedures.

However, it is often challenging to steer a surgical device through the human anatomy. In light of this difficulty, a need exists for surgical devices capable of multiple degrees of articulation.

SUMMARY

In accordance with an embodiment of the present disclosure, there is provided a surgical device for performing surgery. The surgical device includes a handle assembly, an elongate member, an articulation mechanism, and an adapter. The elongate member extends from the handle assembly and has an articulating section and a straight section. The articulating section is configured to articulate with respect to the straight section. The articulation mechanism is operatively associated with the handle assembly and the articulating section. The adapter rotatably couples the elongate member with the articulation mechanism such that when the elongate member is in a first rotational orientation with respect to the articulation mechanism, the articulating section articulates toward a first direction relative to the straight section upon movement of the handle assembly towards the first direction with respect to the straight section. When the elongate member is in a second rotational orientation with respect to the articulation mechanism, the articulating section articulates toward a second direction relative to the straight section upon movement of the handle assembly towards the first direction with respect to the straight section. The first direction is opposite of the second direction.

In an embodiment, the surgical device may further include an end effector operatively coupled to the articulating section of the elongate member.

In another embodiment, the articulation mechanism may include an articulation lock system configured to fix the position of the articulating section with respect to the straight section.

In an embodiment, the elongate member may be coupled with the adapter for concomitant rotation therewith. The articulation mechanism may include a distal seat having a base, an annular flange, and an elongate member extending distally from the base through the annular flange. The elongate member may include a cutout portion defined between side walls. The side walls may define an angle of about 180 degrees. The adapter may include a base sleeve rotatably mounted about the elongate member of the distal seat. The base sleeve may include a stopper extending radially inward from an inner surface of the base sleeve. The stopper may be configured to limit rotation of the adapter.

In another embodiment, the annular flange may define a circumferential groove. The adapter may include a protrusion configured to engage the circumferential groove of the annular flange. In addition, the circumferential groove may include a narrowing portion to secure the protrusion of the adapter therein. The circumferential groove may include a ramp portion that gradually reaches a full depth of the groove.

In another embodiment, the elongate member may define a groove keyed to a protrusion of the adapter for concomitant rotation therewith.

DESCRIPTION OF THE DRAWINGS

Various embodiments of the present disclosure are described hereinbelow with reference to the drawings, wherein:

FIG. 2 is a side view of the surgical device of FIG. 1, illustrating an articulating section in a straight position;

FIG. 3 is a side view of the surgical device of FIG. 1, illustrating the articulating section in an articulated position;

DETAILED DESCRIPTION

Figure 1:
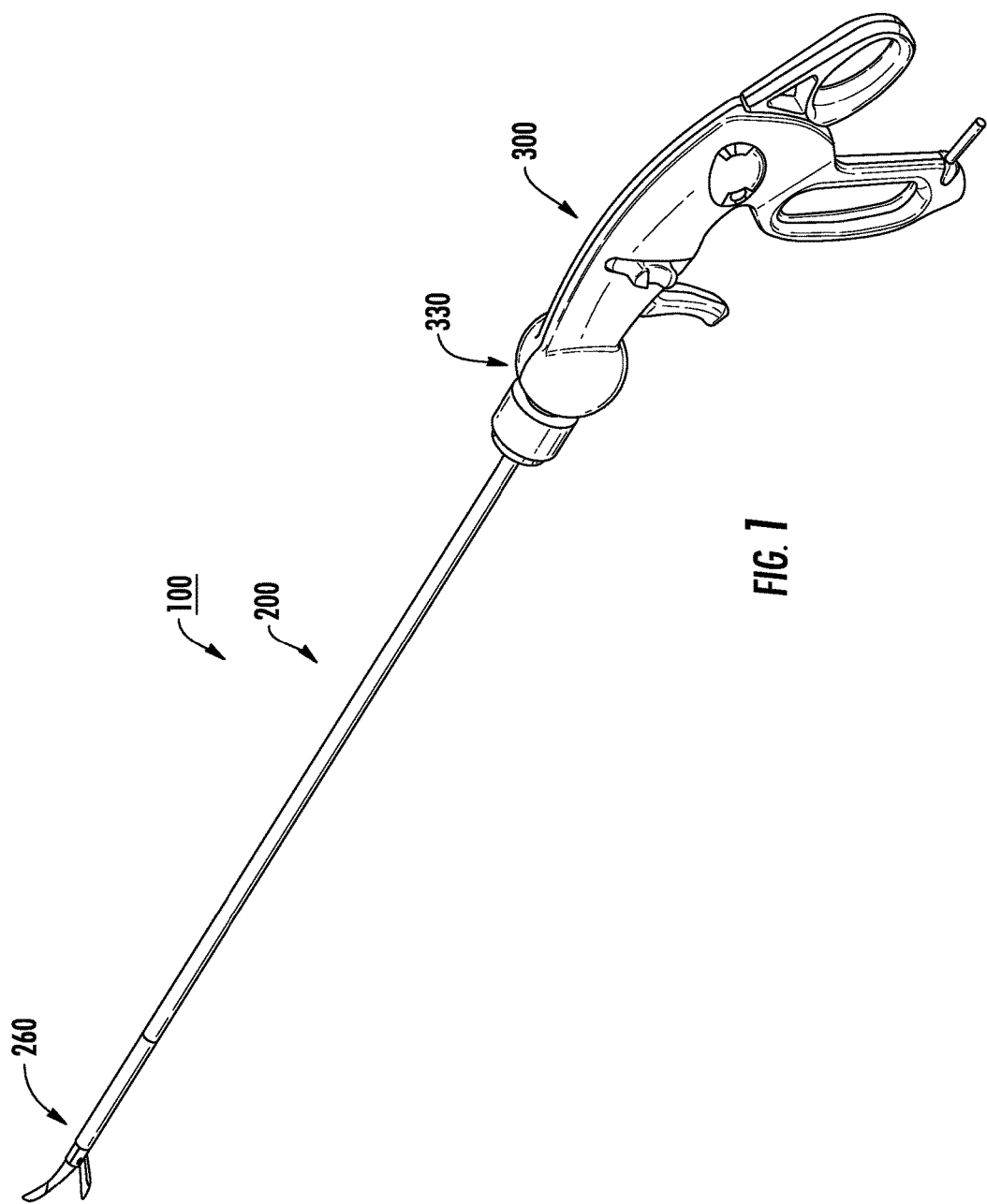
FIG. 1 is a perspective view of a surgical device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference now to FIGS. 1-3, there is illustrated an endoscopic surgical device 100 including an articulation mechanism 330 in accordance with an embodiment of the present disclosure. Surgical device 100 generally includes a handle assembly 300, an endoscopic assembly 200 extending distally from handle assembly 300, and an end effector 260 extending distally from endoscopic assembly 200. Endoscopic assembly 200 includes an articulating section 230 supported on a distal end 214 of elongate outer tube 210. A proximal end 212 of elongate outer tube 210 is coupled with articulation mechanism 330. Elongate outer tube 210 and articulating section 230 are longitudinally aligned with each other along a longitudinal axis "X" when handle assembly 300 is positioned in a neutral position (FIG. 2). Handle assembly 300 is configured to move relative to endoscopic assembly 200. Articulating section 230 is configured to articulate towards a particular direction with respect to elongate outer tube 210 upon movement of handle assembly 300 towards the same or opposite direction with respect to elongate outer tube 210, as will be discussed below. Reference may be made to U.S. Patent Application Publication No. 2010/0030018, the entire contents of which are incorporated herein by reference, for a more detailed discussion of the structure and operation of endoscopic surgical device 100.

Figure 4:
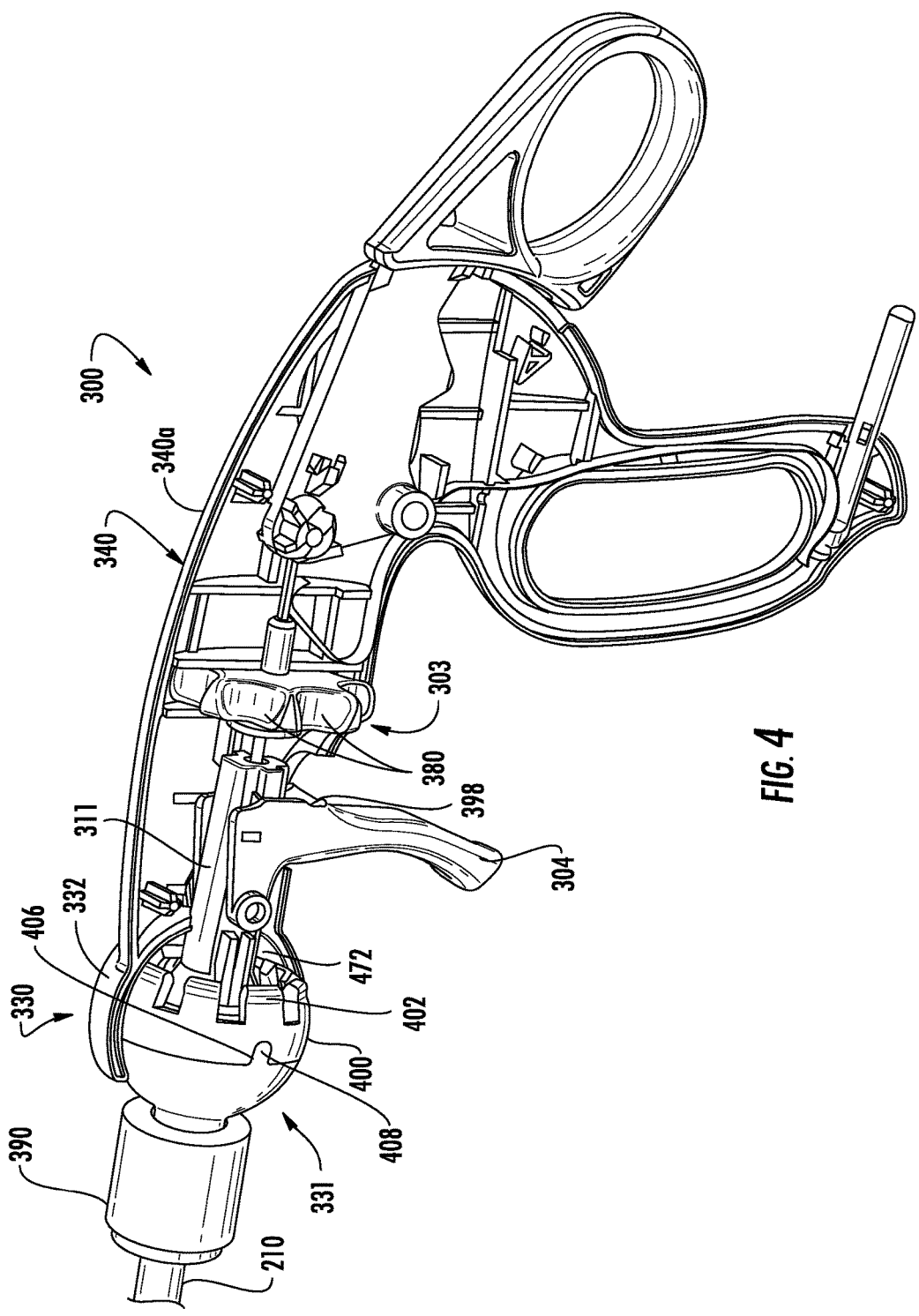
FIG. 4 is a perspective, cutaway view of a handle assembly of the surgical device of FIG. 1, showing the internal components of the handle assembly.
Figure 5:
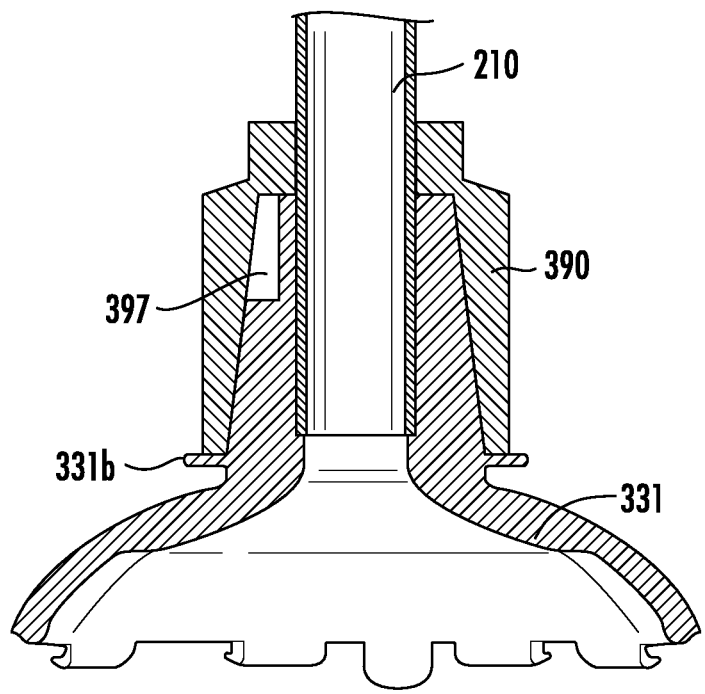
FIG. 5 is a cross-sectional view of a portion of an articulation mechanism of the surgical device of FIG. 1.
Figure 6:
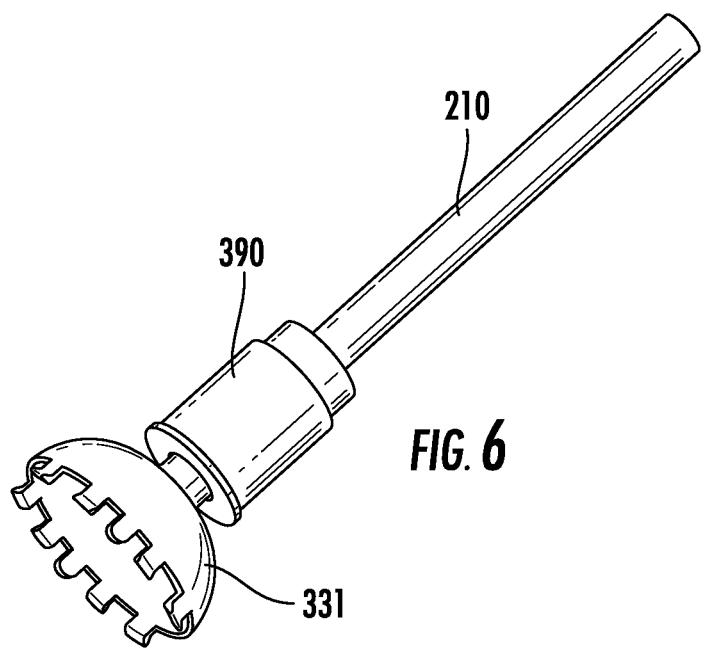
FIG. 6 is a perspective view of the portion of the articulation mechanism of FIG. 5.

With reference to FIGS. 4-6, handle assembly 300 includes a housing 340 including a first half 340a and a second half (not shown) configured to attach to one another. First and second halves 340a collectively form a cup 332 for holding a distal seat or ball 331 of articulation mechanism 330. Elongate outer tube 210 is coupled with an adapter 390 by, e.g., a set screw or adhesive, for concomitant rotation therewith. Adapter 390 is rotatably coupled with distal seat 331.

Figure 7:
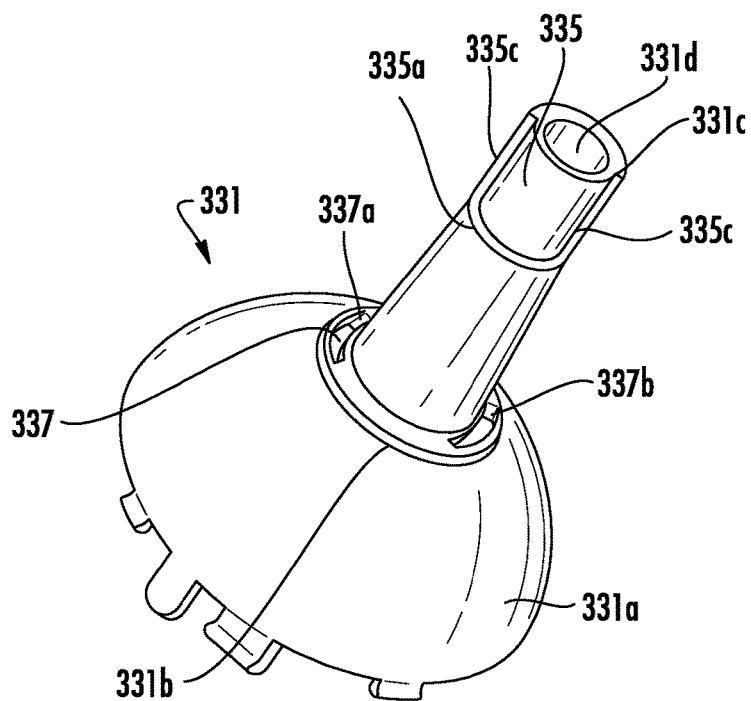
FIG. 7 is a perspective view of a distal seat of the articulation mechanism of FIG. 5.
Figure 8:
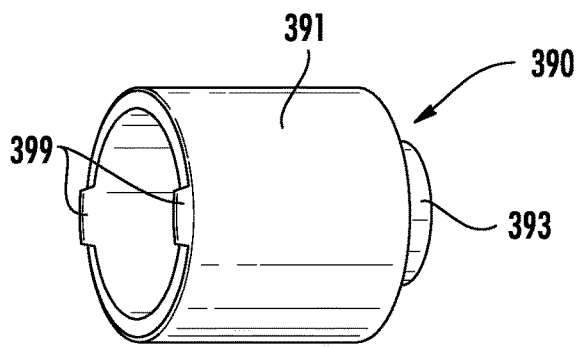
FIG. 8 is a perspective view of an adapter of the articulation mechanism of FIG. 5.
Figure 9:
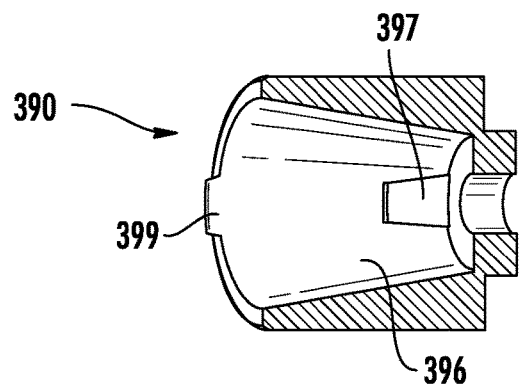
FIG. 9 is a cross-sectional view of the adapter of FIG. 8.

With particular reference now to FIGS. 7-9, distal seat 331 includes a base 331a, an annular flange 331b disposed distal of base 331a, and an elongate member 331c extending distally from base 331a through annular flange 331b. Elongate member 331c defines a bore 331d configured to receive at least a portion of outer tube 210 therein (FIG. 5). Elongate member 331c includes a cutout portion 335 and defines a camming surface 335a. Adapter 390 has a tubular configuration including a base sleeve 391 and a neck portion 393 extending distally from base sleeve 391. Base sleeve 391 is configured and dimensioned to receive at least a portion of elongate member 331c therein. Neck portion 393 is configured and dimensioned to receive at least a portion of outer tube 210 therein. An inner surface 396 of adapter 390 includes a stopper 397 protruding radially inward. Stopper 397 is rotatable within cutout portion 335 defined between side walls 335c. Furthermore, stopper 397 may be configured to slide against camming surface 335a of distal seat 331. In this manner, by limiting the amount of rotation of adapter 390 with respect to distal seat 331, tangling of articulation cables $240_A$, $240_B$, $240_C$, $240_D$ (FIG. 12) is inhibited. For example, cutout portion 335 of distal seat 331 may define an angle of about 180 degrees to limit the amount of rotation of adapter 390 with respect to elongate member 331c of distal seat 331 to about 180 degrees.

Flange 331b of distal seat 331 defines a pair of diametrically opposing grooves 337 configured to receive therein the respective diametrically disposed protrusions 399 on adapter 390. Flange 331b may include a ramp portion 337a that gradually reaches the full depth of groove 337 to facilitates rotation of protrusion 399 into and out of groove 337. Furthermore, groove 337 may include a narrowing portion 337b circumferentially arranged to provide securement of protrusion 399 therein to inhibit rotation of adapter 390 with respect to distal seat 331. In this manner, outer tube 210 is rotatable, for example, to about 180 degrees, with respect to distal seat 331 and can be held in place at that angle by adapter 390.

Figure 10:
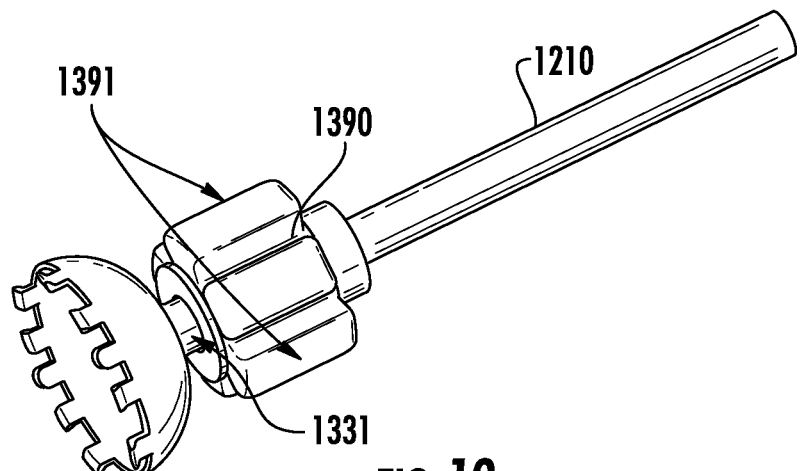
FIG. 10 is a perspective view of a portion of an articulation mechanism of a surgical device in accordance with another embodiment of the present disclosure.
Figure 11:
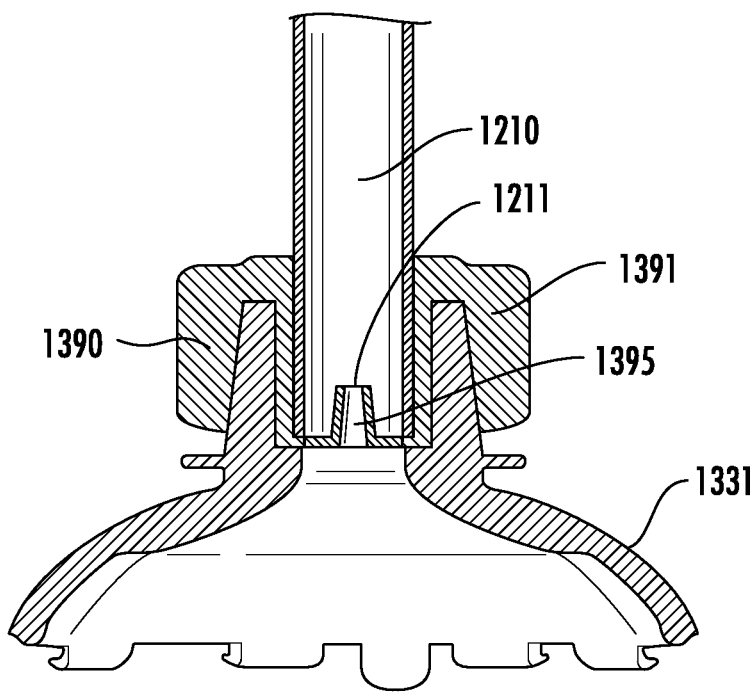
FIG. 11 is a cross-sectional view of the articulation mechanism of FIG. 10.

With reference now to FIGS. 10 and 11, there is illustrated an adapter 1390 in accordance with an embodiment of the present disclosure. Adapter 1390 may include a pair of wing members 1391 to assist the user in rotating adapter 1390 relative to distal seat 1331. Moreover, an outer tube 1210 may define a groove 1211 keyed to a protrusion 1395 of adapter 1390 for concomitant rotation therewith. Under such a configuration, tensions in articulation cables $240_A$, $240_B$, $240_C$, $240_D$ (FIG. 12) may enable outer tube 1210 and adapter 1390 to be held in place.

Figure 12:
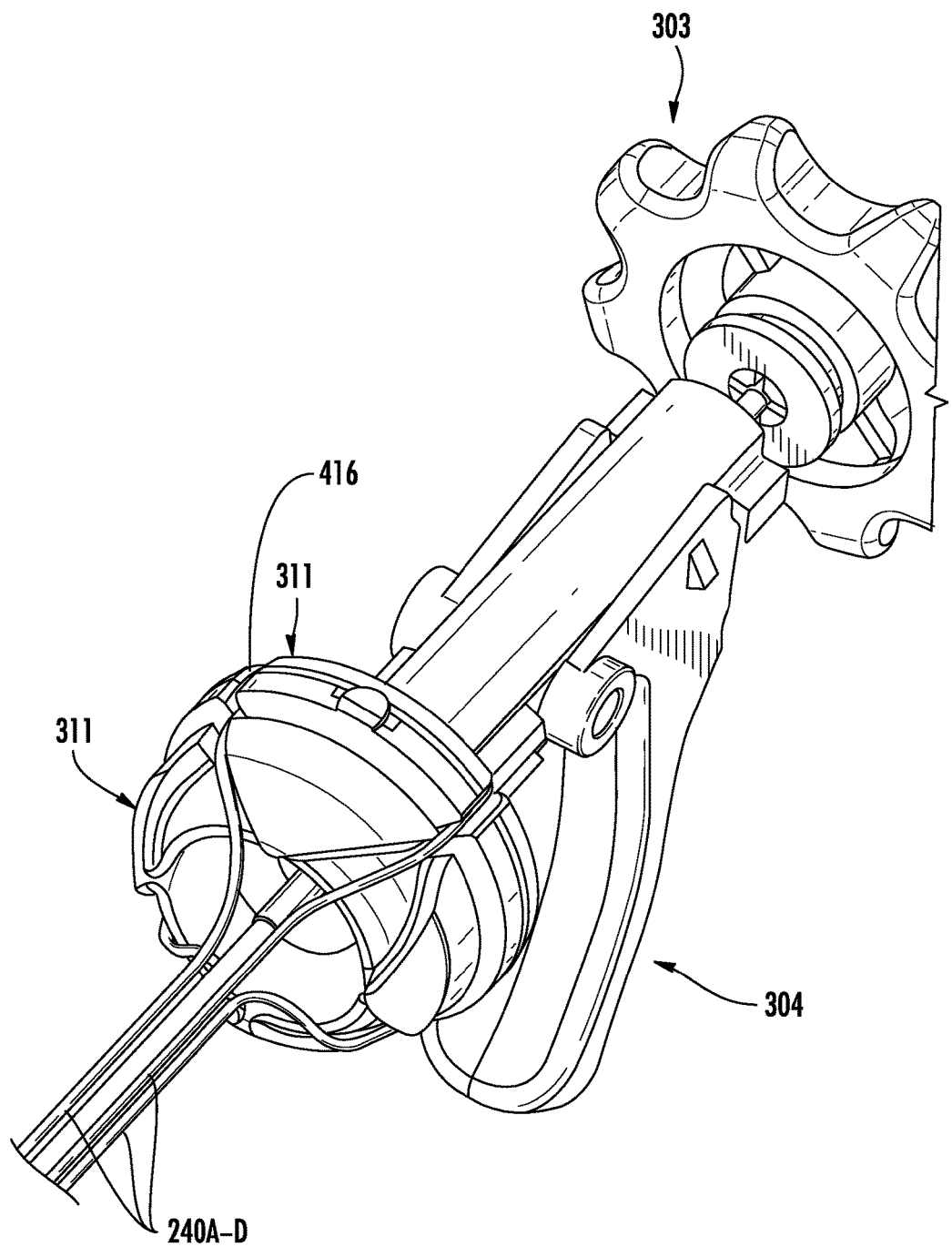
FIG. 12 is a perspective view of a portion of the articulation mechanism of the surgical device of FIG. 1.
Figure 13:
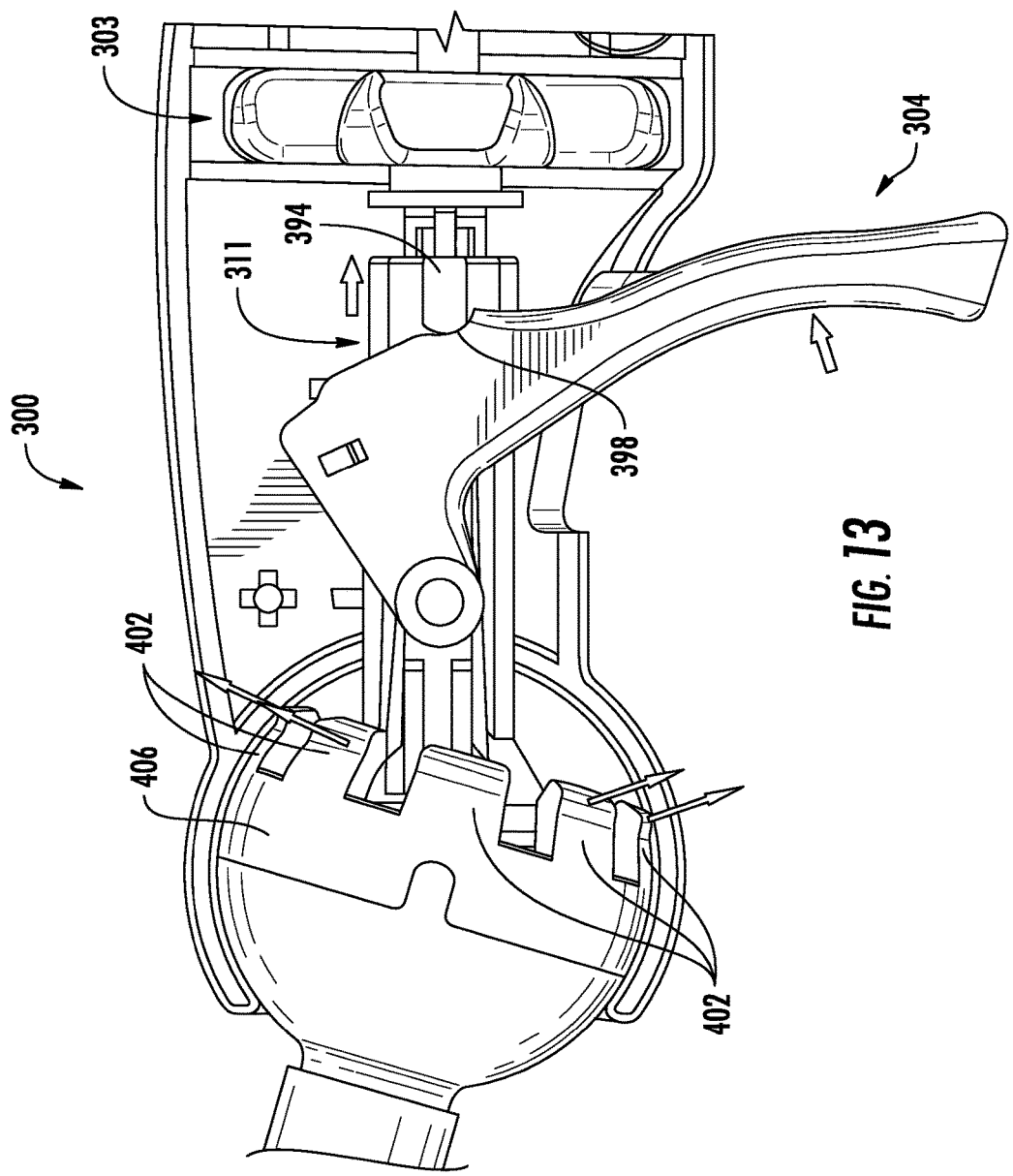
FIG. 13 is a side, cutaway view of a portion of the articulation mechanism of the surgical device of FIG. 1, showing actuation of an articulation lock trigger.

With reference now to FIG. 12, articulation cables $240_A$, $240_B$, $240_C$, $240_D$ are operatively coupled to articulation cable plate 311. Each articulation cable $240_{A-D}$ extends from articulation cable plate 311 to articulating section 230 (FIG. 2) and are operatively coupled therewith. Articulation mechanism 330 includes an articulation lock trigger 304. Articulation lock trigger 304 is operatively coupled to an articulation cable plate 311. When an operator moves articulation lock trigger 304 from the unlocked position toward the locked position, articulation cable plate 311 moves proximally with respect to housing 340 to lock the position of articulating section 230 with respect to elongate outer tube 210. An articulation lock ring 400 (FIG. 4) partially surrounds articulation lock plate 311. Articulation lock ring 400 defines an opening dimensioned to receive articulation lock plate 311 and includes a plurality of locking fingers 402 extending proximally therefrom. Locking fingers 402 are positioned around a periphery of articulation lock ring 400. Articulation lock ring 400 is positioned inside cup 332 of housing 340 and includes two lateral slots 406 disposed in a diametrically opposed relation to each other. Each lateral slot 406 is adapted to receive an extension member 408 of distal seat 331.

Figure 14:
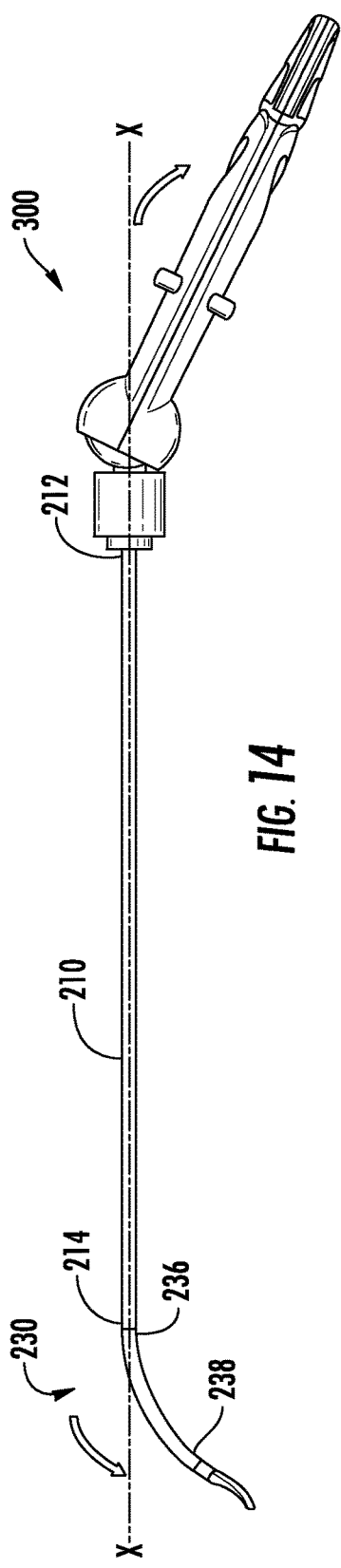
FIG. 14 is a top view of the surgical device of FIG. 1, illustrating the articulating section in an articulated position.

With reference back to FIGS. 4-6, through the rotation of adapter 390 with respect to distal seat 331, articulation cables $240_{A-D}$ may be manipulated to place articulation cables $240_{A-D}$ in a straightened or a crossed configuration. When handle assembly 300 is moved relative to elongate outer tube 210 toward one direction, articulating section 230 articulates toward the same or opposite directions. When articulation cables $240_{A-D}$ are in the straightened configuration, articulation of articulating section 230 mirrors the movement of handle assembly 300 relative to outer tube 210 in opposite direction, and when cables $240_{A-D}$ are in the crossed configuration, articulation of articulating section 230 mirrors the movement of handle assembly 300 relative to outer tube 210 in the same direction. Thus, the operator may adjust the rotational orientation of adapter 390 relative to distal seat 331 prior to and/or during surgery to tailor the surgical device 100 to the surgery being performed. For example, in a crossed configuration, an operator can move handle assembly 300 upwardly relative to elongate outer tube 210 to articulate articulating section 230 upwardly relative to elongate outer tube 210, as depicted in FIG. 3. In addition to this upward motion, the operator can move handle assembly 300 laterally with respect to elongate outer tube 210 to articulate articulating section 230 laterally relative to elongate outer tube 210, as illustrated in FIG. 14.

Figure 15:
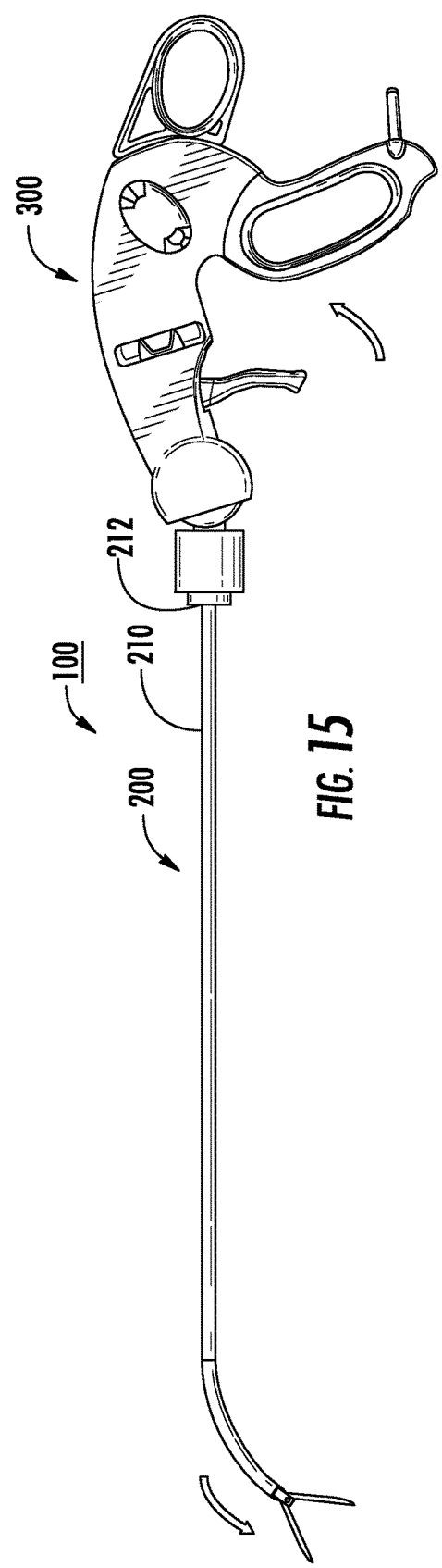
FIG. 15 is a side view of the surgical device of FIG. 1, illustrating the articulating section articulated in a direction opposite of the direction of the handle assembly.
Figure 16:
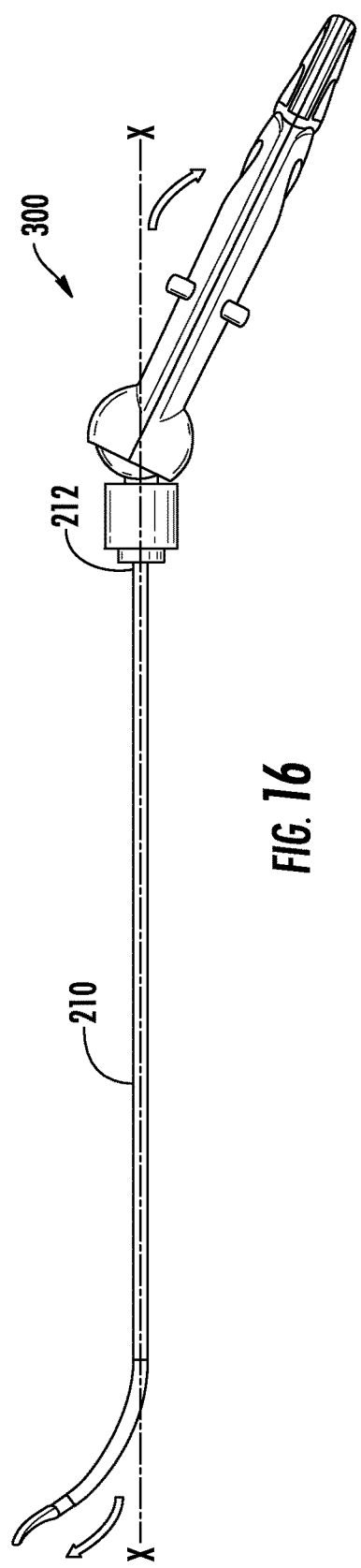
FIG. 16 is a top view of the surgical device of FIG. 1, illustrating the articulating section articulated in a lateral direction opposite of the direction of the handle assembly.

In use, the operator grabs handle assembly 300 and moves the wrist to articulate handle assembly 300 relative to elongate outer tube 210 and distal seat 331. The operator may articulate handle assembly 300 in any direction. Initially, handle assembly 300 may be in a rotational orientation that places articulation cables $240_{A-D}$ in the crossed configuration. Under such a configuration, articulating section 230 mirrors the wrist movement in the same direction (FIGS. 3 and 14). However, adapter 390 may be rotated about 180 degrees with respect to distal seat 331 to place articulation cables $240_{A-D}$ in the straightened configuration, whereby articulating section 230 mirrors the movement of the wrist and articulates relative to elongate outer tube 210 in the opposite direction as handle assembly 300 (FIGS. 15 and 16).

With reference to FIGS. 4 and 12, the operator can fix the desired position of articulating section 230 by actuating articulation lock trigger 304. To actuate articulation lock trigger 304, the operator moves articulation lock trigger 304 toward rotation wheel 303. Upon actuation of articulation lock trigger 304, articulation cable plate 311 is moved in a proximal direction. As articulation cable plate 311 is moved proximally, cable engaging portion 416 pushes fingers 402 of articulation lock ring 400 outwardly toward inner surface 472 of cup 332. When fingers 402 flex outwardly, detents of fingers 402 frictionally engage inner surface 472 of cup 322, thereby locking the position of handle assembly 300 with respect to elongate outer tube 210 and distal seat 331. In addition, the proximal translation of articulation cable plate 311 causes all articulation cables $240_{A-D}$ to move proximally. As a consequence of this proximal motion, all articulation cables 240 are tightened, compressing articulation links (not shown) of articulating section 230 together. Therefore, the compressed articulation links fix the position of articulating section 230 relative to elongate outer tube 210.

Although the illustrative embodiments of the present disclosure have been described herein with reference to the accompanying drawings, the above description, disclosure, and figures should not be construed as limiting, but merely as exemplifications of particular embodiments. While the rotation of adapter 390 was limited to about 180 degrees, it is envisioned that other angles may be selected to better accommodate the operator. Moreover, although the drawings merely show upward and lateral movements of articulating section 230, articulating section 230 has multiple degrees of motion. Irrespective of the specific degrees of motion, the movement of articulating section 230 relative to elongate outer tube 210 mirrors the motion of handle assembly 300 with respect to elongate outer tube 210.

It is to be understood, therefore, that the disclosure is not limited to those precise embodiments, and that various other changes and modifications may be effected therein by one skilled in the art without departing from the scope or spirit of the disclosure.

What is claimed is:

1. A surgical device for performing surgery, comprising:
a handle assembly including a cable plate;
an elongate shaft extending from the handle assembly, the elongate shaft having an articulating section and a straight section, wherein the articulating section is configured to articulate with respect to the straight section;
an articulation mechanism operatively associated with the handle assembly and the articulating section, the articulation mechanism including an elongate member and a plurality of cables, the elongate member including an outer surface defining a circumferential cutout; and
an adapter secured with the elongate shaft for concomitant rotation therewith, the adapter rotatably disposed about the elongate member of the articulation mechanism, the adapter including a stopper engaging the circumferential cutout of the elongate member of the articulation mechanism for a selective range of rotation of the adapter about the elongate member, the plurality of cables interconnecting the articulating section of the elongate shaft and the cable plate of the handle assembly, the adapter transitionable between a first rotational orientation with respect to the articulation mechanism, in which, the plurality of cables is in a crossed configuration such that the articulating section articulates toward a first direction relative to the straight section of the elongate shaft upon movement of the handle assembly towards the first direction and a second rotational orientation with respect to the articulation mechanism, in which, the plurality of cables is in a straight configuration such that the articulating section articulates toward a second direction opposite of the first direction upon movement of the handle assembly towards the first direction.

2. The surgical device according to claim 1, further comprising an end effector operatively coupled to the articulating section of the elongate member.

3. The surgical device according to claim 1, wherein the articulation mechanism includes an articulation lock system configured to fix the position of the articulating section with respect to the straight section.

4. The surgical device according to claim 1, wherein the articulation mechanism further includes a distal seat having a base and an annular flange, the elongate member extending distally from the base through the annular flange.

5. The surgical device according to claim 1, wherein the circumferential cutout defines an angle of about 180 degrees.

6. The surgical device according to claim 1, wherein the adapter includes a base sleeve rotatably mounted about the elongate member of the articulation mechanism.

7. The surgical device according to claim 6, wherein the stopper extends radially inward from an inner surface of the base sleeve.

8. The surgical device according to claim 4, wherein the annular flange defines a circumferential groove.

9. The surgical device according to claim 8, wherein the adapter includes a protrusion configured to engage the circumferential groove of the annular flange.

10. The surgical device according to claim 9, wherein the circumferential groove includes a narrowing portion to secure the protrusion of the adapter therein.

11. The surgical device according to claim 10, wherein the circumferential groove includes a ramp portion that gradually reaches a full depth of the circumferential groove.

12. The surgical device according to claim 1, wherein first and second cables of the plurality of cables diametrically oppose each other.

* * * * *